US008403848B2

(12) United States Patent
Mietus et al.

(10) Patent No.: US 8,403,848 B2
(45) Date of Patent: *Mar. 26, 2013

(54) ASSESSMENT OF SLEEP QUALITY AND SLEEP DISORDERED BREATHING BASED ON CARDIOPULMONARY COUPLING

(75) Inventors: Joseph E. Mietus, Cambridge, MA (US); Chung-Kang Peng, Sharon, MA (US); Robert Joseph Thomas, Newton, MA (US); Ary L. Goldberger, Newton Centre, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 1464 days.

This patent is subject to a terminal disclaimer.

(21) Appl. No.: 12/018,768

(22) Filed: Jan. 23, 2008

(65) Prior Publication Data

US 2008/0119747 A1 May 22, 2008

Related U.S. Application Data

(63) Continuation of application No. 10/846,945, filed on May 17, 2004, now Pat. No. 7,324,845.

(51) Int. Cl.
*A61B 5/00* (2006.01)
*A61B 5/08* (2006.01)
*A61B 5/04* (2006.01)

(52) U.S. Cl. ......... 600/301; 600/484; 600/513; 600/536

(58) Field of Classification Search ........................ None
See application file for complete search history.

(56) References Cited

U.S. PATENT DOCUMENTS

| | | |
|---|---|---|
| 5,105,354 A | 4/1992 | Nishimura |
| 5,902,250 A | 5/1999 | Verrier et al. |
| 6,415,174 B1 | 7/2002 | Bebehani et al. |
| 6,739,335 B1 | 5/2004 | Rapport et al. |
| 7,025,729 B2 | 4/2006 | de Chazal et al. |
| 7,179,229 B1 | 2/2007 | Koh |
| 7,324,845 B2 | 1/2008 | Mietus et al. |

(Continued)

FOREIGN PATENT DOCUMENTS

| | | |
|---|---|---|
| JP | 61-272034 | 12/1986 |
| JP | 64-027535 | 1/1989 |

(Continued)

OTHER PUBLICATIONS

Supplemental European Search Report for European Application No. EP 05 74 9482, European Patent Office, search completed: Jun. 19, 2009, 3 pgs.

(Continued)

*Primary Examiner* — Mark W Bockelman
(74) *Attorney, Agent, or Firm* — Sterne, Kessler, Goldstein & Fox P.L.L.C.

(57) ABSTRACT

An assessment of sleep quality and sleep disordered breathing is determined from the cardiopulmonary coupling between two physiological data series. In an embodiment, an R-R interval series is derived from an electrocardiogram (ECG) signal. The normal beats from the R-R interval series are extracted to produce a normal-to-normal (NN) interval series. The amplitude variations in the QRS complex are used to extract to a surrogate respiration signal (i.e., ECG-derived respiration (EDR)) that is associated with the NN interval series. The two series are corrected to remove outliers, and resampled. The cross-spectral power and coherence of the two resampled signals are calculated over a plurality of coherence windows. For each coherence window, the product of the coherence and cross-spectral power is used to calculate coherent cross power. Using the appropriate thresholds for the coherent cross power, the proportion of sleep spent in CAP, non-CAP, and wake and/or REM are determined.

18 Claims, 5 Drawing Sheets

U.S. PATENT DOCUMENTS

| | | | |
|---|---|---|---|
| 7,440,795 | B2 | 10/2008 | Poezevara |
| 7,734,334 | B2 | 6/2010 | Mietus et al. |
| 2005/0256418 | A1 | 11/2005 | Mietus et al. |
| 2010/0069762 | A1 | 3/2010 | Mietus et al. |

FOREIGN PATENT DOCUMENTS

| | | |
|---|---|---|
| JP | 2004-159888 | 6/2004 |
| WO | WO 98/43536 | 10/1998 |
| WO | WO 2004/026133 A2 | 4/2004 |

OTHER PUBLICATIONS

Raymond B. et al., "Screening for Obstructive Sleep Apnoea Based on the Electrocardiogram—The Computer in Cardiology Challenge" *Computers in Cardiology*, vol. 27, pp. 267-270 (2000).

Redmond S. et al., "Electrocardiogram-Based Automatic Sleep Staging in Sleep Disordered Breathing" *Computers in Cardiology*, vol. 30, pp. 609-612 (2003).

Unbehaun a. et al., "Interaction of heart-rate fluctuations and respiration in 12 to 14-year-old children during sleeping and waking" *Journal of the Autonomic Nervous System*, vol. 57, pp. 141-143 (1996).

Office Action for Canadian Application No. 2,566,193, mailed Feb. 24, 2012, 3 pgs.

Japanese Official Action for Japanese Application No. 2007-527323, mailed Mar. 14, 2011, 3 pgs.

English translation of Japanese Official Action Application No. 2007-527323, mailed Mar. 14, 2011, 4 pgs.

English-language bibliographic data for: Hideaki, Y., JP 61-272034 (listed on accompanying PTO /SB/08A as document FP3) (English-language abstract not available).

English-language abstract for: Toshihiro, N., JP 64-027535 (listed on accompanying PTO/SB/08A as document FP4).

Australian Official Action for Australian Application No. 2006269263, dated Mar. 9, 2011, 3 pgs.

Aljadeff, G. et al., "Heart Rate Variability in Children With Obstructive Sleep Apnea," Sleep, vol. 20, No. 2, pp. 151-157 (Feb. 1997).

Benitez, D. et al., "The use of the Hilbert transform in ECG signal analysis," *Computers in Biology and Medicine*, vol. 31, pp. 399-406 (2001).

Blasi, A. et al., "Cardiovascular variability after arousal from sleep: time-varying spectral analysis," *Journal of Applied Physiology*, vol. 95, No. 4, pp. 1394-1404 (Oct. 2003).

Boland, L.L. et al., "Measures of cognitive function in persons with varying degrees of sleep-disordered breathing: the Sleep Heart Health Study," *Journal of Sleep Research*, vol. 11, pp. 265-272 (2002).

Buchheit, M. et al., "Effect of increased training load on vagal-related indexes of heart rate variability: a novel sleep approach," *American Journal of Physiology*, vol. 287, No. 6, Part 2, pp. H2813-H2818 (Dec. 2004).

Carter, N. et al., "Cardiovascular and Autonomic Response to Environmental Noise During Sleep in Night Shift Workers," Sleep, vol. 25, No. 4, pp. 457-464 (Jun. 15, 2002).

Chervin, R.D. And Aldrich, M.S., "The Relation Between Multiple Sleep Latency Test Findings and the Frequency of Apneic Events in REM and Non-REM Sleep," Chest, vol. 113, No. 4, pp. 980-984 (Apr. 1998).

Chervin, R.D. et al., "Inattention, Hyperactivity, and Symptoms of Sleep-Disordered Breathing," Pedriatics, vol. 109, No. 3, pp. 449-456 (Mar. 2002).

Chesson, A.L. Jr. et al., "The Indications for Polysomnography and Related Procedures," Sleep, vol. 20, No. 6, pp. 423-487 (Jun. 1997).

Cohen, J., *Statistical Power Analysis for the Behavioral Sciences*, 2nd ed, Lawrence Erlbaum Associates, Hillsdale, NJ, pp. vii-ix, xi-xv, xvii-xxi, 1-17, and 559-567 (1988).

Collop, N. A., "Scoring variability between polysomnography technologists in different sleep laboratories," *Sleep Medicine*, vol. 3, pp. 43-47 (2002).

Cornolo, J. et al., "Autonomic control of the cardiovascular system during acclimatization to high altitude: effects of sildenafil," *Journal of Applied Physiology*, vol. 97, No. 3, pp. 935-940 (Sep. 2004).

de Chazal, P. et al., "Automated Processing of the Single-Lead Electrocardiogram for the Detection of Obstructive Sleep Apnoea," *IEEE Transactions on Biomedical Engineering*, vol. 50, No. 6, pp. 686-696 (Jun. 2003).

De Gennaro, L. et al., "The Cyclic Alternating Pattern Decreases as a Consequence of Total Sleep Deprivation and Correlates with EEG Arousals," *Neurpsychobiology*, vol. 45, No. 2, pp. 95-98 (Mar. 2002).

Dingli, K. et al., "Spectral oscillations of RR intervals in sleep apnoea/hypopnoea syndrome patients," *European Respiratory Journal*, vol. 22, No. 6, pp. 943-950 (Dec. 2003).

Dumont, M. et al., "Interdependency between heart rate variability and sleep EEG: linear/non-linear?," *Clinical Neurophysiology*, vol. 115, No. 9, pp. 2031-2040 (May 18, 2004).

Dworschak, M. et al., "The use of spectral measures of heart rate variability to differentiate between male snorers and patients with sleep apnoea syndrome," *Anaesthesia*, vol. 56, No. 5, pp. 424-428 (May 2001).

Engleman, H.M. et al., "Cognitive Function in the Sleep Apnea/Hypopnea Syndrome (SAHS)," Sleep, vol. 23, Supplement 4, pp. S102-S108 (Jun. 15, 2000).

Farina, B. et al., "Microstructure of sleep in depressed patients according to the cyclic alternating pattern," *Journal of Affective Disorders*, vol. 77, Issue 3, pp. 227-235 (Dec. 2003).

Ferini-Strambi, L. et al., "The impact of cyclic alternating pattern on heart rate variability during sleep in healthy young adults," *Clinical Neurophysiology*, vol. 111, pp. 99-101 (2000).

Ferini-Strambi, L. et al., "Heart Rate Variability during Sleep in Snorers with and without Obstructive Sleep Apnea," Chest, vol. 102, No. 4, pp. 1023-1027 (Oct. 1992).

Goldberger, A.L. et al., "PhysioBank, PhysioToolkit, and PhysioNet: Components of a New Research Resource for Complex Physiological Signals," Circulation, pp. 1-6 (Jun. 13, 2000).

Gottlieb, D. J. et al., "Symptoms of Sleep-Disordered Breathing in 5-Year-Old Children Are Associated With Sleepiness and Problem Behaviors," Pediatrics, vol. 112, No. 4, pp. 870-877 (Oct. 2003).

Gottlieb D,J. et al., "Does Snoring Predict Sleepiness Independently of Apnea and Hypopnea Frequency?" *American Journal of Respiratory and Critical Care Medicine*, vol. 162, No. 4, pp. 1512-1517 (Oct. 2000).

Gottlieb, D.J. et al., "Relation of Sleepiness to Respiratory Disturbance Index: The Sleep Heart Health Study," *American Journal of Respiratory and Critical Care Medicine*, vol. 159, No. 2, pp. 502-507 (Feb. 1999).

Gozal, D. "Sleep-Disordered Breathing and School Performance in Children," Pediatrics, vol. 102, No. 3, Part 1, pp. 616-620 (Sep. 1998).

Greene, M.G. And Carroll, J.L., "Consequences of sleep-disordered breathing in childhood," *Current Opinion in Pulmonary Medicine*, vol. 3, No. 6, pp. 456-463 (Nov. 1997).

Guilleminault, C. et al., "Cyclical Variation of the Heart Rate in Sleep Apnoea Syndrome: Mechanisms, and Usefulness of 24 h Electrocardiography as a Screening Technique," *The Lancet*, vol. I, No. 8369, pp. 126-131 (Jan. 21, 1984).

Gula, L.J. et al., "Heart Rate Variability in Obstructive Sleep Apnea: A Prospective Study and Frequency Domain Analysis," *A.N.E.*, vol. 8, No. 2, pp. 144-149 (Apr. 2003).

Halász, P. et al., "The nature of arousal in sleep," *Journal of Sleep Research*, vol. 13, pp. 1-23 (2004).

Hilton, M.F. et al., "Evaluation of frequency and time-frequency spectral analysis of heart rate variability as a diagnostic marker of the sleep apnoea syndrome," *Medical & Biological Engineering & Computing*, vol. 37, No. 6, pp. 760-769 (Nov. 1999).

Iellamo, F. et al., "Baroreflex Buffering of Sympathetic Activation During Sleep: Evidence From Autonomic Assessment of Sleep Macroarchitecture and Microarchitecture," *Hypertension*, vol. 43, No. 4, pp. 814-819 (Apr. 2004).

Khoo, M.C.K. et al., "Spectral Indices of Cardiac Autonomic Function in Obstructive Sleep Apnea," Sleep, vol. 22, No. 4, pp. 443-451 (Jun. 15, 1999).

Kingshott, R.N. et al., "Does arousal frequency predict daytime function?," *European Respiratory Journal*, vol. 12, No. 6, pp. 1264-1270 (Dec. 1998).

Kuo, T.B., "Scatterplot Analysis of EEG Slow-Wave Magnitude and Heart Rate Variability: An Integrative Exploration of Cerebral Cortical and Autonomic Functions," *Sleep*, vol. 27, No. 4, pp. 648-656 (Jun. 15, 2004).

Lieberman, H.R. et al., "Effects of caffeine, sleep loss, and stress on cognitive performance and mood during U.S. Navy Seal training," *Psychopharmacology*, vol. 164, pp. 250-261 (2002).

Lipsitz, L.A. et al., "Heart rate and respiratory rhythm dynamics on ascent to high altitude," *British Heart Journal*, vol. 74, No. 4, pp. 390-396 (Oct. 1995).

Lord, S. et al., "Interrater Reliability of Computer-Assisted Scoring of Breathing during Sleep," *Sleep*, vol. 12, No. 6, pp. 550-558 (Dec. 1989).

Manser, R.L. et al., "Impact of Different Criteria for Defining Hypopneas in the Apnea-Hypopnea Index," *Chest*, vol. 120, No. 3, pp. 909-914 (Sep. 2001).

Margel, D. et al., "Long-Term Intermittent Exposure to High Ambient $CO_2$ Causes Respiratory Disturbances During Sleep in Submariners," *Chest*, vol. 124, No. 5, pp. 1716-1723 (Nov. 2003).

Mark, R.G. and Moody, G.B., "Arrhythmia Analysis, Automated," *Encyclopedia of Medical Devices and Instrumentation*, vol. 1, pp. 120-130 (1988).

Mendelson, W.B., "The Relationship of Sleepiness and Blood Pressure to Respiratory Variables in Obstructive Sleep Apnea," *Chest*, vol. 108, No. 4, pp. 966-972 (Oct. 1995).

Meoli, a.L. et al., "Hypopnea in Sleep-Disordered Breathing in Adults," *Sleep*, vol. 24, No. 4, pp. 469-470 (Jun. 15, 2001).

Mietus, J.E. et al., "Detection of Obstructive Sleep Apnea from Cardiac Interbeat Interval Time Series," *Computers in Cardiology*, vol. 27, pp. 753-756 (Sep. 24-27, 2000).

Mietus, J.E. et al., "The pNNx-files: re-examining a widely-used heart rate variability measure," *Heart*, vol. 88, No. 4, pp. 378-380 (Oct. 2002).

Miyashita, T. at al., "Spectral analyses of electroencephalography and heart rate variability during sleep in normal subjects," *Autonomic Neuroscience: Basic and Clinical*, vol. 103, pp. 114-120 (2003).

Moldofsky, H., "Management of sleep disorders in fibromyalgia," *Rheumatic Disease Clinics of North America*, vol. 28, No. 2, pp. 353-365 (May 2002).

Moody, G.B. And Mark, R.G., "Development and Evaluation of a 2-Lead ECG Analysis Program," *Computers in Cardiology*, pp. 39-44 (Oct. 12-15, 1982).

Moody, G.B. at al., "Clinical Validation of the ECG-Derived Respiration (EDR) Technique," *Computers in Cardiology*, pp. 507-510 (Oct. 7-10, 1986).

Moody, G.B. et al., "Derivation of Respiratory Signals From Multi-Lead ECGs," *Computers in Cardiology*, pp. 113-116 (Sep. 8-11, 1985).

Park, H. J . et al., "Automated Detection and Elimination of Periodic ECG Artifacts in EEG Using the Energy Interval Histogram Method," *IEEE Transactions on Biomedical Engineering*, vol. 49, No. 12, pp. 1526-1533 (Dec. 2002).

Parrino, L. et al., "Cyclic alternating pattern (CAP) in normal sleep: polysomnographic parameters in different age groups," *Electroencephalography and Clinical Neurophysiology*, vol. 107, No. 6, pp. 439-450 (Dec. 1998).

Parrino, L. et al., "Effects of prolonged wakefulness on cyclic alternating pattern (CAP) during sleep recovery at different circadian phases," *Journal of Sleep Research*, vol. 2, pp. 91-95 (1993).

Parrino, L. et al., "Is insomnia a neurophysiological disorder? The role of sleep EEG microstructure," *Brain Research Bulletin*, vol. 63, No. 5, pp. 377-383 (Jun. 30, 2004).

Parrino, L. et al., "Multidrug Comparison (Lorazepam, Triazolam, Zolpidem, and Zopiclone) in Situational Insomnia: Polysomnographic Analysis by Means of the Cyclic Alternating Pattern," *Clinical Neuropharmacology*, vol. 20, No. 3, pp. 253-263 (Jun. 1997).

Parrino, L. et al., "Sleep reactivity during acute nasal CPAP in obstructive sleep apnea syndrome," *Neurology*, vol. 54, No. 8, pp. 1633-1640 (Apr. 25, 2000).

Peled, N. et al., "Contributions of Hypoxia and Respiratory Disturbance Index to Sympathetic Activation and Blood Pressure in Obstructive Sleep Apnea Syndrome," *American Journal of Hypertension*, vol. 11, No. 11, Part 1, pp. 1284-1289 (Nov. 1998).

Penzel, T., "Is heart rate variability the simple solution to diagnose sleep apnoea?" *European Respiratory Journal*, vol. 22, pp. 870-871 (2003).

Penzel, T. et al., "Comparison of Detrended Fluctuation Analysis and Spectral Analysis for Heart Rate Variability in Sleep and Sleep Apnea," *IEEE Transactions on Biomedical Engineering*, vol. 50, No. 10, pp. 1143-1151 (Oct. 2003).

Penzel, T. et al., "Dynamics of Heart Rate and Sleep Stages in Normals and Patients with Sleep Apnea," *Neuropsychopharmacology*, vol. 28, Suppl. 1, pp. S48-S53 (Jul. 2003).

Penzel, T. et al., "Systematic comparison of different algorithms for apnoea detection based on electrocardiogram recordings," *Medical & Biological Engineering & Computing*, vol. 40, No. 4, pp. 402-407 (Apr. 2002).

"Practice Parameters for the Indications for Polysomnography and Related Procedures," *Sleep*, vol. 20, No. 6, pp. 406-422 (Jun. 1997).

Raschke, F., "Arousals and Aircraft Noise—Environmental Disorders of Sleep and Health in Terms of Sleep Medicine," *Noise Health*, vol. 6, pp. 15-26 (2004).

Rechtschaffen, A. And Kales, A. (eds.), *A manual of standardized terminology, techniques and scoring system for sleep stages of human subjects*, UCLA Brain Information Service, pp. 1-14 (1968).

Redline, S. et al., "The Effects of Age, Sex, Ethnicity, and Sleep-Disordered Breathing on Sleep Architecture," *Archives of Internal Medicine*, vol. 164, pp. 406-418 (Feb. 23, 2004).

Rizzi, M. et al., "Cyclic Alternating Pattern: A New Marker of Sleep Alteration in Patients with Fibromyalgia," *Journal of Rheumatology*, vol. 31, No. 6, pp. 1193-1199 (Jun. 2004).

Roche, F. et al., "Cardiac Interbeat Interval Increment for the Identification of Obstructive Sleep Apnea," *PACE*, vol. 25, No. 8, pp. 1192-1199 (Aug. 2002).

Roche, F. et al., "Predicting sleep apnoea syndrome from heart period: a time-frequency wavelet analysis," *European Respiratory Journal*, vol. 22, No. 6, pp. 937-942 (Dec. 2003).

Roche, F. et al., "Screening of Obstructive Sleep Apnea Syndrome by Heart Rate Variability Analysis," *Circulation*, vol. 100, No. 13, pp. 1411-1415 (Sep. 28, 1999).

Roehrs, T. et al., "Predictors of Objective Level of Daytime Sleepiness in Patients with Sleep-Related Breathing Disorders," *Chest*, vol. 95, No. 6, pp. 1202-1206 (Jun. 1989).

Sateia, M.J., "Neuropsychological impairment and quality of life in obstructive sleep apnea," *Clinics in Chest Medicine*, vol. 24, No. 2, pp. 249-259 (Jun. 2003).

Schaefer, K.E. et al., "Effect of 18-h watch schedules on circadian cycles of physiological functions during submarine patrols," *Undersea Biomedical Research*, vol. 6, Supplement: Preventive Aspects of Submarine Medicine, pp. S81-S90 (1979).

Shamsuzzaman, A.S.M. et al., "Obstructive Sleep Apnea: Implications for Cardiac and Vascular Disease," *Journal of the American Medical Association*, vol. 290, No. 14, pp. 1906-1914 (Oct. 8, 2002).

Shiomi, T. et al., "Augmented Very Low Frequency Component of Heart Rate Variability During Obstructive Sleep Apnea," vol. 19, No. 5, pp. 370-377 (Jun. 1996).

Shouldice, R.B. et al., "Detection of Obstructive Sleep Apnea in Pediatric Subjects using Surface Lead Electrocardiogram Features," *Sleep*, vol. 27, No. 4, pp. 784-792 (Jun. 15, 2004).

Stein, P.K. et al., "A Simple Method to Identify Sleep Apnea Using Holter Recordings," *Journal of Cardiovascular Electrophysiology*, vol. 14, No. 5, pp. 467-473 (May 2003).

Stoilova, I.M. et al., "How Human Sleep in Space—Investigations During Space Flights," *Advances in Space Research*, vol. 31, No. 6, pp. 1611-1615 (2003).

Stradling, J.R. and Davies, R.J.O., "Sleep • 1: Obstructive sleep apnoea/hypopnoea syndrome: definitions, epidemiology, and natural history," *Thorax*, vol. 59, No. 1, pp. 73-78 (Jan. 2004).

Tateishi, O. et al., "Apnea-Related Heart Rate Variability in Congestive Heart Failure Patients," *Clinical and Experimental Hypertension*, vol. 25, No. 3, pp. 183-189 (2003).

Terzano, M.G. And Parrino, L., "Origin and Significance of the Cyclic Alternating Pattern (CAP)," *Sleep Medicine Reviews*, vol. 4, No. 1, pp. 101-123 (Feb. 2000).

Terzano, M.G. et al., "Atlas, rules, and recording techniques for the scoring of cyclic alternating pattern (CAP) in human sleep," *Sleep Medicine*, vol. 2, No. 6, pp. 537-553 (Nov. 2001).

Terzano, M.G. et al., "Atlas, rules, and recording techniques for the scoring of cyclic alternating pattern (CAP) in human sleep," *Sleep Medicine*, vol. 3, pp. 187-199 (2002).

Terzano, M.G. et al., "CAP variables and arousals as sleep electroencephalogram markers for primary insomnia," *Clinical Neurophysiology*, vol. 114, No. 9, pp. 1715-1723 (2003).

Terzano, M.G. et al., "The Cyclic Alternating Pattern as a Physiologic Component of Normal NREM Sleep," *Sleep*, vol. 8, No. 2, pp. 137-145 (Jun. 1985).

Terzano, M.G. et al., "Modifications of sleep structure induced by increasing levels of acoustic perturbation in normal subjects," *Electroencephalography & Clinical Neurophysiology*, vol. 76, No. 1, pp. 29-38 (Jul. 1990).

Terzano, M.G. et al., "Polysomnographic Analysis of Arousal Responses in Obstructive Sleep Apnea Syndrome by Means of the Cyclic Alternating Pattern," *Journal of Clinical Neurophysiology*, vol. 13, No. 2, pp. 145-155 (Mar. 1996).

"The Report of an American Academy of Sleep Medicine Task Force: Sleep-Related Breathing Disorders in Adults: Recommendations for Syndrome Definition and Measurement Techniques in Clinical Research," *Sleep*, vol. 22, No. 5, pp. 667-689 (1999).

Thomas, R.J., "Cyclic alternating pattern and positive airway pressure titration," *Sleep Medicine*, vol. 3, pp. 315-322 (2002).

Thomas, R.J., "Flow-limitation and sleep: exploring the interface of a complex and dynamic system," *Sleep Medicine*, vol. 2, pp. 375-377 (2002).

Tsai, W.H. et al.," a Comparison of Apnea-Hypopnea Indices Derived from Different Definitions of Hypopnea," *American Journal of Respiratory and Critical Care Medicine*, vol. 159, No. 1, pp. 43-48 (Jan. 1999).

Viola, A.U. et al., "Sleep as a Tool for Evaluating Autonomic Drive to the Heart in Cardiac Transplant Patients," *Sleep*, vol. 27, No. 4, pp. 641-647 (Jun. 15, 2004).

Whitney, C.W. et al., "Reliability of Scoring Respiratory Disturbance Indices and Sleep Staging," *Sleep*, vol. 21, No. 7, pp. 749-757 (Nov. 1, 1998).

Wolk, R. and Somers, V.K., "Cardiovascular consequences of obstructive sleep apnea," *Clinics in Chest Medicine*, vol. 24, No. 2, pp. 195-205 (Jun. 2003).

Yang, C.C.H. et al., "Relationship between electroencephalogram slow-wave magnitude and heart rate variability during sleep in rats," *Neuroscience Letters*, vol. 336, No. 1, pp. 21-24 (2003).

Younes, M., "Contributions of Upper Airway Mechanics and Control Mechanisms to Severity of Obstructive Apnea," *American Journal of Respiratory and Critical Care Medicine*, vol. 168, No. 6, Part 1, pp. 645-658 (Sep. 15, 2003).

Young, T. et al., "Epidemiology of Obstructive Sleep Apnea: A Population Health Perspective," *American Journal of Respiratory and Critical Care Medicine*, vol. 165, No. 9, pp. 1217-1239 (May 1, 2002).

Lipsitz, L.A. et al., "Heart Rate and Respiratory Rhythm Dynamics on Ascent to High Altitude," *British Heart Journal* 74(4):390-396 (Oct. 1995), http://heart.bmjjournals.com/cgi/content/abstract/74/4/390 (printed Apr. 25, 2005, 2 pages).

Moody, G.B. et al., "Clinical Validation of the ECG-Derived Respiration (EDR) Technique," Computers in Cardiology 1986, vol. 13, IEEE Computer Society Press, Washington, D.C., pp. 507-510, http://www.physionet.org/physiotools/edr/cic86/edr86.html (printed Apr. 12, 2005, 6 pages).

Moody, G., B., "Derive A Respiration Signal From an ECG," Feb. 13, 1986 (last revised: Jan. 21, 2004), http://www.physionet.org/physiotools/edr/edr.c (printed Apr. 12, 2005, 6 pages).

Moody, G.B. et al., "Derivation of Respiratory Signals From Multi-Lead ECGs," Computers in Cardiology 1985, vol. 12, IEEE Computer Society Press, Washington, D.C., pp. 113-116, http://www.physionet.org/physiotools/edr/cic85/edr85.html, (printed Apr. 12, 2005, 8 pages).

Moody, G.B., "ECG-Derived Respiration," http://www.physionet.org/physiotools/edr/, (printed Apr. 12, 2005, 2 pages).

International Search Report and Written Opinion from International Appl. No. PCT/US06/26591, 8 pages, dated Apr. 2, 2007.

Supplementary European Search Report for European Application No. EP 06 78 6669, European Patent Office, 8 pages, dated Aug. 13, 2010.

Vijendra, S. et al., "Frequency Domain Analysis of Heart Rate Variability in Sleep Disordered Breathing," *IEEE EMBS*, 1:208-211, Sep. 17, 2003.

Japanese Official Action for Japanese Application No. 2008-521475, mailed Nov. 2, 2011, 3 pgs.

English translation of Japanese Official Action for Japanese Application No. 2008-521475, mailed Nov. 2, 2011, 5 pgs.

English-language abstract for: Onishi, H., JP 2004-159888 (listed on accompanying PTO/SB/08a as document FP5), 1 pg.

Office Action for European Application No. 06 786 669.9, mailed Apr. 12, 2012, 5 pgs.

Office Action for U.S. Appl. No. 12/570,163, mailed Aug. 1, 2012, 7 pgs.

ASSESSMENT OF SLEEP QUALITY AND SLEEP DISORDERED BREATHING BASED ON CARDIOPULMONARY COUPLING

CROSS-REFERENCE TO RELATED APPLICATION

This application is a continuation of U.S. application Ser. No. 10/846,945, filed May 17, 2004, which issued as U.S. Pat. No. 7,324,845, on Jan. 29, 2008, the entire disclosure of which is herein incorporated by reference.

STATEMENT REGARDING FEDERALLY-SPONSORED RESEARCH OR DEVELOPMENT

Part of the work performed during development of this invention utilized U.S. Government funds. The U.S. Government has certain rights in this invention.

BACKGROUND OF THE INVENTION

1. Field of the Invention

The present invention relates generally to analyzing physiologic data, and more specifically, to non-invasively assessing sleep pathology and physiology from coherence measurements.

2. Related Art

At least five percent of the general population suffers from medically significant sleep disorders, the most common being sleep-disordered breathing (also known as sleep apnea). As a major public health concern, sleep disorders contribute to excessive daytime sleepiness and the associated risks of driving accidents, hypertension, heart attacks, strokes, depression, and attention deficit disorders. The prevalence of sleep disorders is much higher (exceeding thirty percent) in select populations such as, individuals having obesity, congestive heart failure, diabetes, and renal failure.

Conventional diagnostic systems for detecting sleep disorders typically involve complex multiple channel recordings in a sleep laboratory and labor intensive scoring, which collectively lead to substantial expense and patient discomfort. An example of a conventional sleep diagnostic system is a full polysomnograph. Polysomnography is the gold standard for detection and quantification of sleep-disordered breathing, and includes sleep staging, scoring of respiratory abnormality (e.g., apneas, hypopneas, flow-limitation, periodic breathing, and desaturation episodes), and limb movements. Typical markers of sleep disorder severity are the sleep fragmentation index, the apnea-hypopnea index, the respiratory disturbance index, an arousal frequency or index, and the oxygen desaturation index.

One of the many limitations of conventional sleep diagnostic systems is the dependence on tedious manual scoring of "events" based on physiologically arbitrary criteria. Only a moderate correlation can be found between these events and cognitive and cardiovascular outcomes. As such, conventional systems leave a significant amount of unexplained variance in effect, and fail to adequately describe the physiologic impact of sleep disorders. Therefore, a quantitative measure that evaluates the impact of sleep disorders on sleep physiology could be useful in clarifying some of the unexplained variance. A continuous biomarker of physiological state may be particularly useful to follow treatment effects. A continuous biomarker may also be useful to discriminate those in whom the seemingly subtle sleep disorder disease is physiologically disruptive. Such physiologically disruptive settings include primary snoring, which in adults, is associated with excessive sleepiness, and in children, is associated with inattentive and/or hyperactive behaviors.

Presently, rapid and accurate throughput of sleep diagnostics does not exist, despite the development of limited forms of sleep testing that include various combinations of airflow, respiratory effort, electrocardiogram (ECG), and oximetry. This is especially problematic in conditions such as congestive heart failure and chronic renal failure, where severe and complex forms of sleep apnea may adversely affect both mortality and morbidity. Since conventional sleep studies are so expensive, information on sleep effects are typically limited in the pre-approval assessments of drugs used in neurological and psychiatric practice.

Therefore, a need exists to develop a technology that can provide a simple, inexpensive, repeatable measure of the presence and impact of a variety of sleep disruptive stimuli (such as noise, pain, drugs, mood disorders, disordered breathing) on sleep state physiology and stability.

SUMMARY OF THE INVENTION

The present invention provides a method, system and computer program product for performing a quantitative analysis of cardiopulmonary coupling between two physiological signals to detect and evaluate sleep physiology and pathology. According to embodiments of the present invention, an R-R interval series is combined with a corresponding respiration signal to determine the coherent cross-power of these two signals.

In an embodiment, an electrocardiogram (ECG) signal is used to derive the R-R interval series. In another embodiment, the R-R interval series is acquired from another type of physiological signal representing heart rate dynamics within a subject. Thus, the heart rate physiological signal can be derived from, for example, ECG, blood pressure, pulse Doppler flow (e.g., sensed via ultrasound recording), ECG signal from another electrical signal (e.g., electroencephalographic (EEG)), or the like.

In an embodiment, the same ECG is used to derive a surrogate respiration signal (i.e., ECG-derived respiration (EDR)). In another embodiment, the respiration signal is acquired from another type of physiological signal representing respiration dynamics in the subject. Thus, the respiration physiological signal can be derived from, for example, ECG, nasal thermistor, nasal flow, chest band, abdominal band, or the like.

In an embodiment using ECG to derive the R-R intervals and associated respiration signal, an automated beat detection routine or function detects beats from the ECG and classifies them as either normal or ectopic. In addition, amplitude variations in the QRS complex due to shifts in the cardiac electrical axis relative to the electrodes during respiration are determined. From these amplitude variations, the EDR is obtained.

A time series of normal-to-normal (NN) intervals and the time series of the EDR associated with the NN intervals are then extracted from the R-R interval series. Outliers due to false detections or missed detections are removed using a sliding window average filter, and the resulting NN interval series and its associated EDR are resampled.

The cross-spectral power and coherence of the two resampled signals are calculated over a predefined window using the Fast Fourier Transform (FFT) or Discrete Fourier Transform (DFT). The coherence window is thereafter advanced, and the FFT or DFT calculations are repeated until the entire NN interval series and associated EDR series have been analyzed.

For each coherence window, the product of the coherence and cross-spectral power is used to calculate the ratio of coherent cross power in the low frequency (i.e., 0.01-0.1 Hz.) band to that in the high frequency (i.e., 0.1-0.4 Hz.) band. An excess of coherent cross power in the low frequency band is associated with periodic characteristics in multiple physiological systems. In the electroencephalogram, this is reflected by the morphology called Cyclic Alternating Pattern (CAP), characterized by the presence of repetitive activation complexes (K-complexes, delta waves, variable bursts of alpha or beta rhythms) alternating with relatively quiescent "B" or baseline phases. In the respiratory system, periodically recurring cycles of abnormal respiration that may or may not be obstructed are seen.

A preponderance of coherent cross-power in the high frequency band is associated with normal sinus arrhythmia and is the ECG marker of this state. There is also a close correlation between high-frequency coherent cross-power and the EEG morphology called non-CAP.

Using the ratio of power in the very low frequency (i.e., 0-0.01 Hz) band to the combined coherent cross power in the low and high frequency bands allows detection of wake and/or REM. An excess of coherent cross-power in the very low frequency band tends to be associated with wake and/or REM.

As such, the present invention provides an ECG-based measure of sleep quality and sleep disordered breathing using the CAP/non-CAP physiological concept. Using the appropriate thresholds for the coherent cross power ratios, the proportion of sleep spent in CAP, non-CAP, and wake and/or REM can be determined.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable one skilled in the pertinent art(s) to make and use the invention. In the drawings, generally, like reference numbers indicate identical or functionally or structurally similar elements. Additionally, generally, the leftmost digit(s) of a reference number identifies the drawing in which the reference number first appears.

DETAILED DESCRIPTION OF THE INVENTION

According to embodiments of the present invention, a method, system, and computer program product is provided to perform a quantitative analysis of cardiopulmonary coupling between two physiological signals to detect and evaluate sleep physiology.

Sleep is a complex state characterized by cycling stages (i.e., rapid eye movement (REM) sleep and non-REM sleep) and a sequence of progressive and regressive depths (i.e., stages I to IV in non-REM sleep). There is also a stability dimension that has been recognized, but not generally applied in clinical practice, based on the concept of cyclic alternating pattern (CAP) in non-REM sleep. CAP-type non-REM sleep is unstable, whereas, non-CAP non-REM sleep is a restful, non-aroused state with a stabilizing influence.

The distribution of stages and states of sleep can be altered by numerous sleep disrupting extrinsic factors (e.g., noise, heat, cold, vibration, barotraumas, motion, gravitational stress, etc.) and intrinsic factors (e.g., disordered breathing, pain, seizures, restless legs, periodic limb and related movements, etc.). More importantly, these factors all induce CAP, a state characterized by periodic behavior in multiple measures (such as, brain electrical activity, heart rate, respiration, and blood pressure). In the non-CAP state, physiological stability exists.

Sleep disordered breathing (SDB) is associated with the emergence of relatively low frequency (i.e., 0.01 to 0.1 Hertz (Hz)) periodic behavior in multiple physiologic systems, such as respiration, heart rate, and electroencephalographic (EEG) activity. These pathological oscillations represent periods of physiologically unstable sleep behavior and low frequency coupling of respiration-driven ECG variability. In this state, the EEG pattern typically displays CAP attributes.

In contrast, periods of stable breathing are associated with the non-CAP EEG pattern and high frequency (i.e., 0.1 to 0.4 Hz) coupling between respiration and beat-to-beat heart rate variability (e.g., respiratory sinus arrhythmia). In patients with SDB, spontaneous and relatively abrupt transitions tend to occur between these two states.

As described in greater detail below, the present invention provides techniques and/or methodologies for quantifying cardiopulmonary coupling, which shows a strong correlation with CAP and non-CAP states. Accordingly, the present invention provides a biomarker of sleep physiology and pathology, such as the percentage of sleep spent in periods of unstable sleep behavior.

Figure 1:
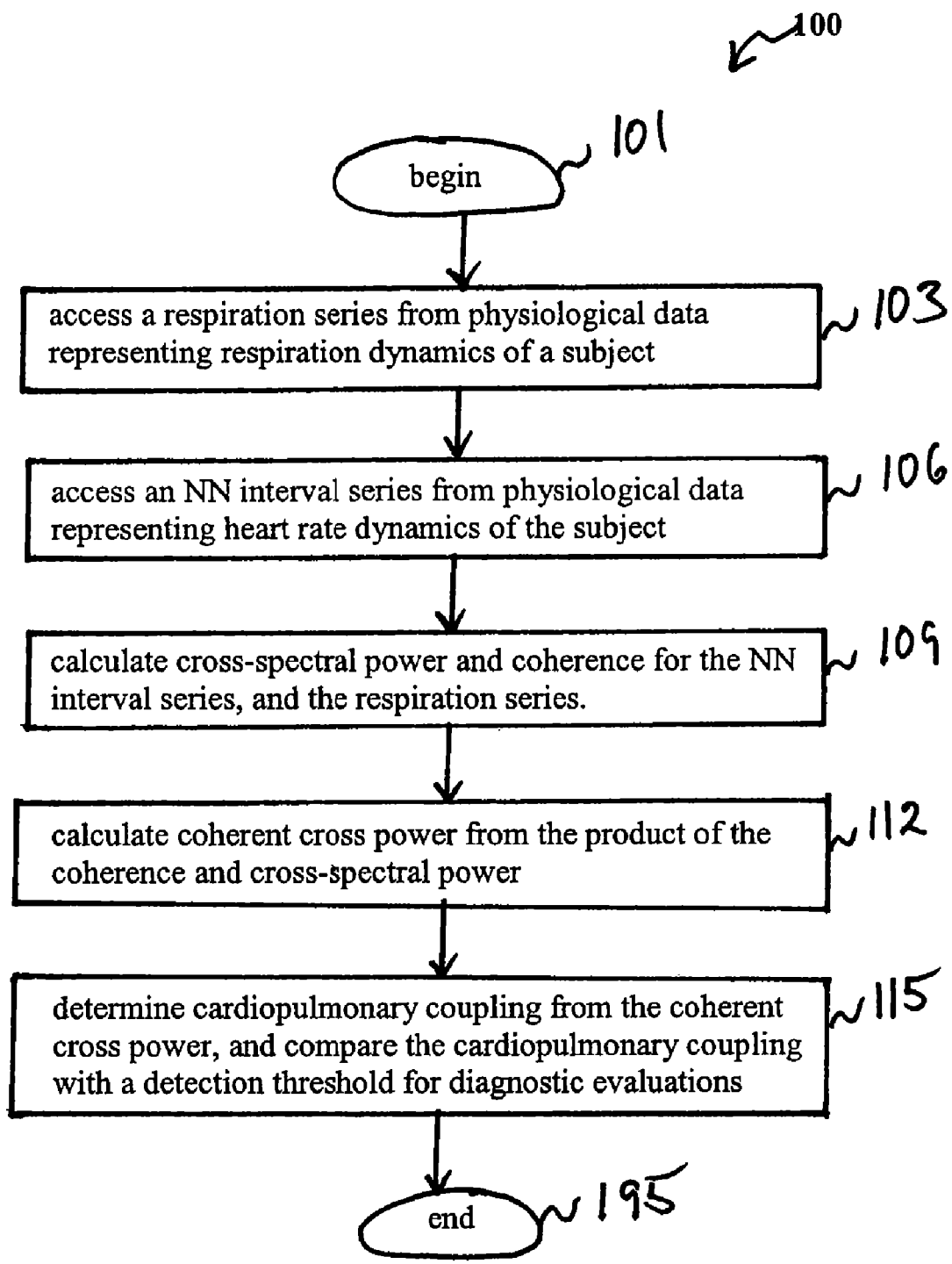
FIG. 1 illustrates an operational flow for detecting cardiopulmonary coupling according to an embodiment of the present invention.

Referring to FIG. 1, flowchart 100 represents the general operational flow of an embodiment of the present invention. More specifically, flowchart 100 shows an example of a control flow for detecting cardiopulmonary coupling from a subject (such as, a patient, test/laboratory subject, or the like).

The control flow of flowchart 100 begins at step 101 and passes immediately to step 103. At step 103, a set of interval respiration data (referred to herein as a "respiration series") is accessed from a physiological signal. The physiological signal can be an electrocardiogram (ECG or EKG), from which a surrogate respiratory signal is obtained, as described in greater detail below. However, the physiological signal can be any type of signal representing respiration dynamics in the subject. As such, the respiration data series can be derived from, for example, a nasal thermistor, forced oscillation, acoustic reflectance techniques, nasal-cannula pressure transducer system, impedance/inductance/piezo chest and/or abdominal effort band, or the like.

At step 106, a set of interval heart rate data (referred to herein as a "R-R interval series") is accessed from a physiological signal. In an embodiment, the heart rate physiological signal is the same physiological signal that provides the respiration interval signal that is described above at step 103. In another embodiment, the heart rate physiological signal is distinct from the physiological signal that provides the respiration signal. Moreover, the heart rate physiological signal can be the same type of signal (e.g., both being ECG) or a different type of signal (e.g., ECG for the heart rate interval series, and nasal-cannula pressure-transducer nasal thermistor flow for the respiration series) as the physiological signal that provides the respiration signal.

Accordingly, the heart rate physiological signal is any type of signal that enables the derivation of a series of heart rate interval data (i.e., R-R intervals or R-R equivalent intervals). Thus, the heart rate physiological signal can be any type of signal representing heart rate dynamics in the subject. Such signal can be derived from, for example, ECG, blood pressure, pulse Doppler flow (e.g., sensed via ultrasound recording), ECG signal from another electrical signal (e.g., EEG), or the like.

Regardless of their source(s), the heart rate interval series and respiration series must be temporally aligned to determine the cardiopulmonary coupling. In an embodiment, the normal sinus (N) beats are selected from the heart rate interval series to produce a series of normal-to-normal (NN) heart rate data (referred to herein as an "NN interval series"). The respiration series would therefore be temporally aligned with the NN interval series.

At step 109, cross-spectral power and coherence is calculated using both the heart rate interval series (or NN interval series) and respiration series. At step 112, the product of the coherence and cross-spectral power calculations are taken to derive a set of coherent cross power calculations. At step 115, the coherent cross power calculations are used to determine the cardiopulmonary coupling. As described in greater detail below, the cardiopulmonary coupling can be compared with one or more detection thresholds for diagnostic evaluations, such as SDB screening or the like. Afterwards, the control flow ends as indicated at step 195. As such, the present invention provides for a fully automated quantitative analysis of cardiopulmonary coupling that can be used, for example, to screen for SDB, assess physiological impacts of SDB, and/or monitor the therapeutic effects of different approaches to treating SDB, or the like.

Figure 2:
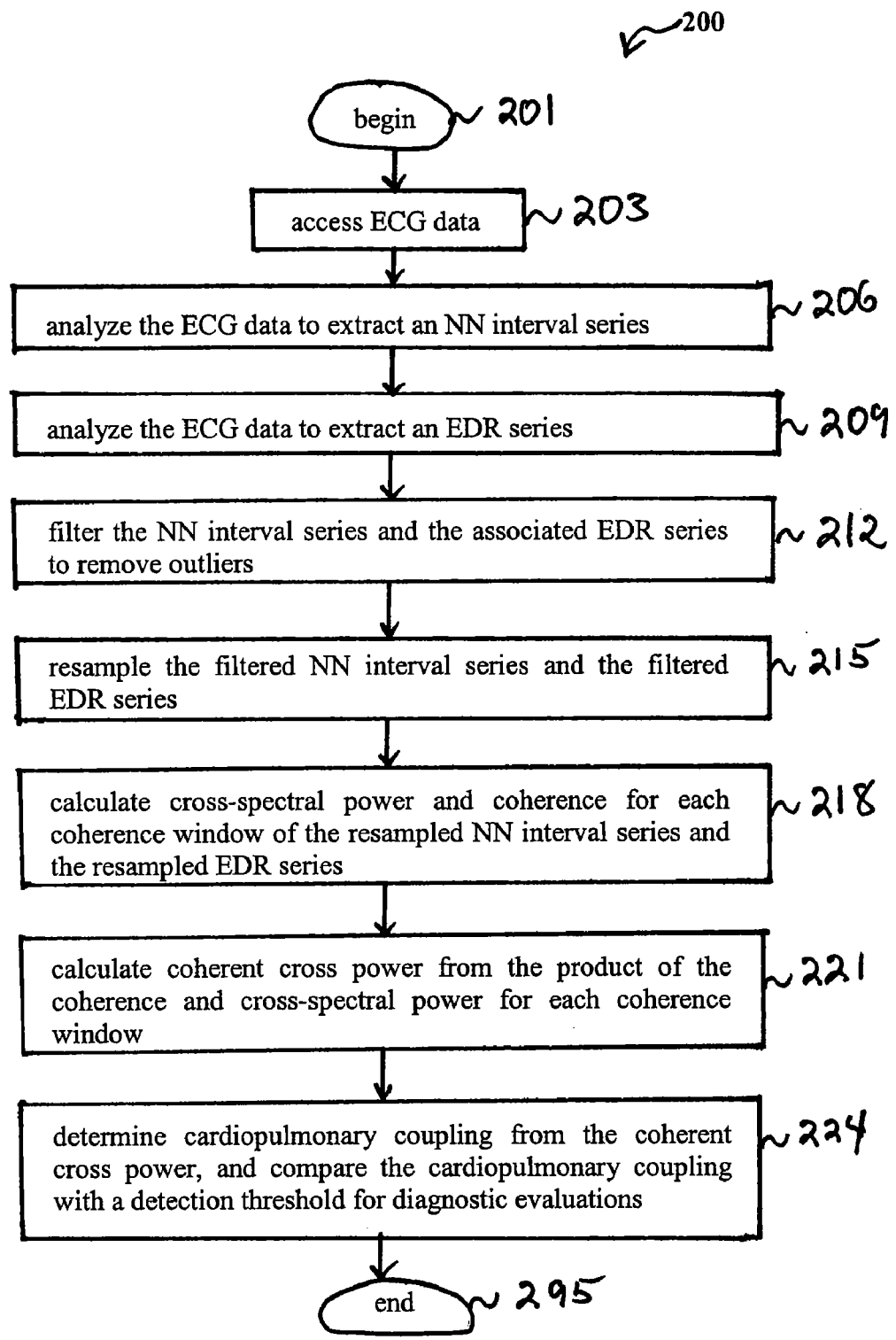
FIG. 2 illustrates an operational flow for using ECG-derived respiration to quantify cardiopulmonary coupling according to an embodiment of the present invention.

Referring to FIG. 2, flowchart 200 represents the general operational flow of another embodiment of the present invention. More specifically, flowchart 200 shows an example of a control flow for quantifying cardiopulmonary coupling by using ECG-derived respiration (EDR) to integrate R-R variability and fluctuations in cardiac electrical axis associated with respiration.

The control flow of flowchart 200 begins at step 201 and passes immediately to step 203. At step 203, an ECG signal or set of ECG data is accessed. In an embodiment, surface ECG data is retrieved from a storage medium. In another embodiment, surface ECG data is obtained directly from an ECG monitoring device. For example, ECG data can be obtained, in real time or otherwise, from a Holter monitor or recording from an ECG monitor available from GE Marquette Medical Systems (Milwaukee, Wis.).

In an embodiment, a single or two lead ECG signal is obtained directly from an ECG monitoring device. If using one lead, the skin sensor or electrode should be placed at or near the V2 chest position. If using two leads, it is preferable to position the electrodes relatively orthogonal to each other. However, other chest positions can be used to obtain the single or two lead ECG data.

At step 206, the ECG data is analyzed to detect and classify heart beats (i.e., R-R intervals), from the ECG data, as being normal (N) or ectopic. In an embodiment, an automated beat detection and annotation routine or function is used to process digitized ECG data from a Holter recording. The routine detects and classifies (i.e., labels) the heart beats from the digitized data. The output is a time series of annotated heart beats (i.e., "R-R interval series"). This series is then processed to retain only normal-to-normal sinus beats (i.e., "NN interval series").

At step 209, the ECG data is analyzed to extract a time series of QRS amplitude variations (i.e., "EDR series") that are associated with the NN interval series. The amplitude variations in the QRS complex (from the normal beats) are due to shifts in the cardiac electrical axis relative to the electrodes during respiration. From these amplitude variations, a surrogate respiratory signal (i.e., EDR) is derived. In an embodiment, the same function or routine used to extract the NN interval series is also used to measure the QRS amplitudes for the heart beats, and produce a continuous EDR signal.

At step 212, the NN interval series and the associated EDR series are analyzed to detect and/or remove any outliers due to false detections or missed detections. For example, during step 206, the automated beat detection function may generate a false detection or fail to detect a normal data point for the NN interval series (and, hence the associated EDR series). In an embodiment, a sliding window average filter is used to remove the outliers, as described with reference to FIG. 3 in greater detail below.

At step 215, the filtered NN interval series and the filtered EDR series are resampled. The resampling rate depends on the subject class, and is selected to optimize the data series for the spectra calculations described in the following steps. For example, for human subjects, both series are resampled at two Hz. For premature or neonatal subjects (who are approximately less than one year of age), a four Hz resampling rate is used because neonatal infants typically have a heart rate that is approximately twice the rate of an adult. For nonhuman subjects (such as, laboratory mice), a twenty Hz resampling rate is used.

At step 218, cross-spectral power and coherence are calculated for overlapping windows of data selected from, both, the resampled NN interval series and the resampled EDR series. In an embodiment, a Fast Fourier Transform (FFT) is used to compute the cross-spectral power and coherence calculations for the two signals. As described in greater detail below with reference to FIG. 4, a plurality of overlapping windows is used to perform the FFT computations.

At step 221, a data series of "coherent cross power" are calculated from the product of the coherence and cross-spectral power calculations from step 218. For each window, the product of the coherence and cross-spectral power is used to calculate the coherent cross power for each window of data.

If a coherent cross power calculation falls within the range of 0 to 0.01 Hz, it is considered to be within the very low frequency (VLF) band. If the coherent cross power falls within the range of 0.01 to 0.1 Hz, it is considered to be within the low frequency (LF) band. If the coherent cross power falls within the range of 0.1 to 0.4 Hz, it is considered to be within the high frequency (HF) band. When making the VLF, LF, and HF determinations, at least two frequency bins in each band is used to make the calculations. The two bins having the greatest power are used.

At step 224, "cardiopulmonary coupling" is determined from the coherent cross power. The cardiopulmonary coupling can be compared with a detection threshold for a variety of diagnostic applications. For example, the cardiopulmonary coupling can be compared with a predefined detection threshold to detect or evaluate sleep qualities, such as CAP activity, non-CAP activity, wake and/or REM activity, or the like.

For CAP activity, the coherent cross power is used to calculate a ratio of coherent cross power in the LF band to that in HF. An excess of coherent cross power in the low frequency band is associated with periodic behaviors in the EEG (i.e., CAP) and periodic patterns of breathing. In an embodiment, the detection thresholds are 0.2 for the minimum LF power, and 2.0 for the minimum LF/HF ratio.

For non-CAP, the coherent cross power is used to calculate a ratio of coherent cross power in the LF band to that in HF. An excess of coherent cross power in the high frequency band is associated with physiologic respiratory sinus non-CAP) arrhythmia, stable non-periodic breathing patterns and non-CAP EEG. In an embodiment, the detection thresholds are 0.02 for the minimum HF power, and 1.5 for the maximum LF/HF ratio.

For wake and/or REM activity, the ratio of coherent cross power in the VLF band to combined power in LF and HF allows detection of wake and/or REM. An excess of coherent cross power in the VLF band tends to be associated with wake and/or REM. In an embodiment, the detection thresholds are 0.05 for the minimum VLF power and 0.2 for the maximum VLF-to-(LF+HF) ratio.

In those with significant sleep-disordered breathing, REM sleep usually has coherent cross power characteristics very similar and often indistinguishable from CAP physiology. Cardiopulmonary coupling can also be used to detect or evaluate SDB and its impact on sleep (e.g., the proportion of sleep time spent in CAP). For SDB, the coherent cross power is used to calculate a ratio of coherent cross power in the LF band to that in HF. An excess of coherent cross power in the LF band is associated with CAP, periodic respiration, and EEG CAP. In an embodiment, the detection thresholds are 0.2 for the minimum LF power, and 50 for the minimum LF/HF ratio.

Cardiopulmonary coupling can also be used to assess physiological impacts of the aforesaid sleep qualities, SDB, or the like. The cardiopulmonary coupling can also be used monitor the therapeutic effects of different approaches to treating the aforesaid sleep qualities, SDB, or the like. Hence, as described above, the present invention combines the use of mechanical and autonomic effects of, for example, SDB on ECG parameters. Upon completion of the cardiopulmonary coupling quantification and analyses, the control flow ends as indicated at step 295.

Figure 3:
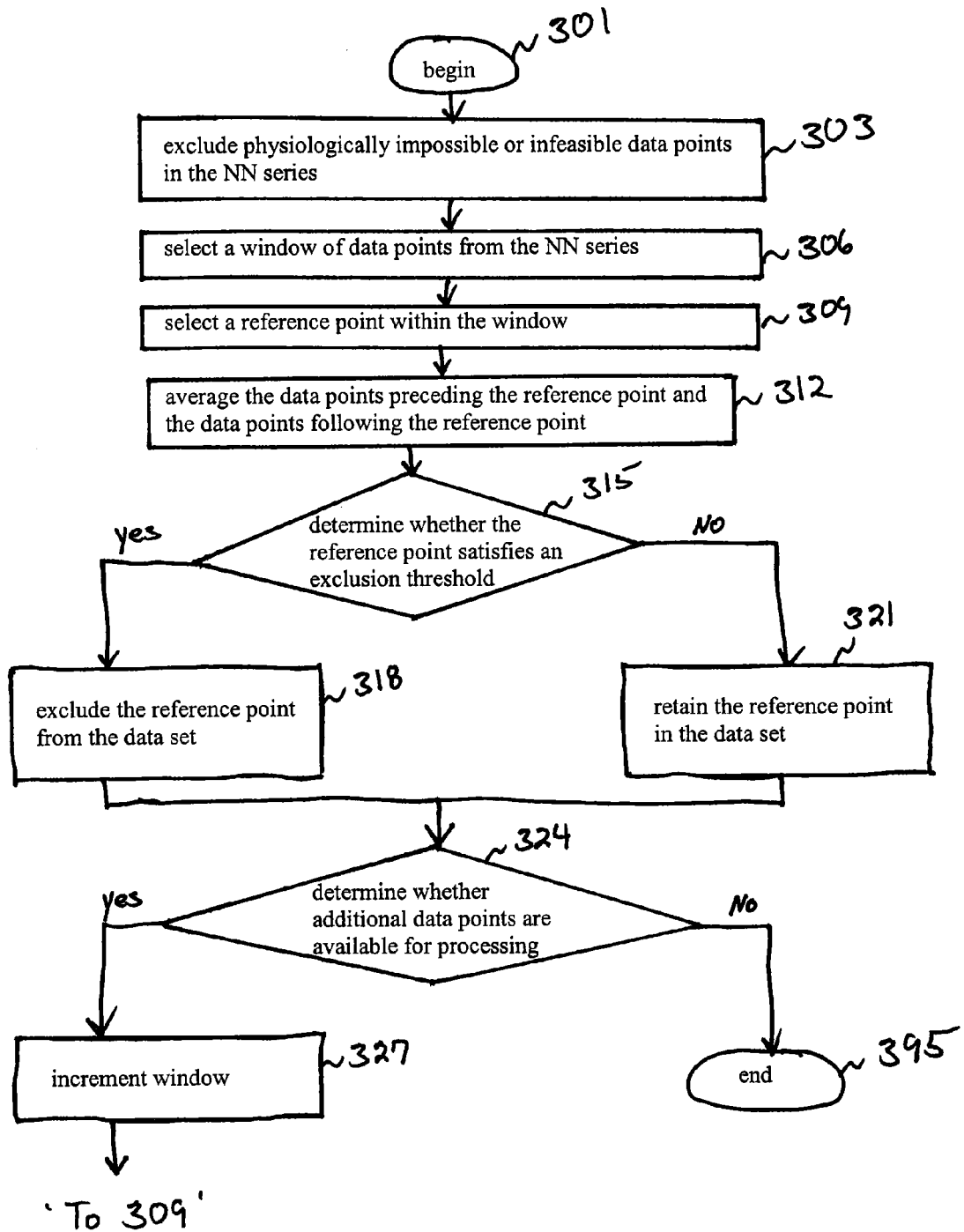
FIG. 3 illustrates an operational flow for removing outliers from a data interval series according to an embodiment of the present invention.

As described above with reference to step 212, in an embodiment, the NN interval series and their associated EDR series are analyzed to detect and/or remove outliers due to false detections or missed detections. Referring to FIG. 3, flowchart 300 represents the general operational flow of an embodiment of the present invention for removing outliers from a data series. More specifically, flowchart 300 shows an example of a control flow for using a sliding window average to filter outliers.

The control flow of flowchart 300 begins at step 301 and passes immediately to step 303. At step 303, all data points in the NN interval series that are determined to be physiologically impossible or infeasible are excluded a priori. The a priori exclusion threshold differs according to the subject class. In an embodiment, the a priori exclusion threshold is an NN interval less than 0.4 seconds or an NN interval greater than 2.0 seconds.

At step 306, the window size is set to begin the averaging. In an embodiment, the window size is set for forty-one data points. Next, a first window (i.e., a first set of forty-one data points) are selected from the NN series.

At step 309, a reference point is selected from within the window. For example, the middle (or twenty-first) data point can be selected as the reference point.

At step 312, the twenty points preceding the reference point and the twenty points following the reference point are averaged. At step 315, it is determined whether the reference point equals or exceeds a predefined threshold based on the average value calculated at step 312. In an embodiment, the reference point exclusion threshold is set at twenty percent.

At step 318, the reference point is excluded from the data series if it satisfies the reference point exclusion threshold. For example, if the reference point exclusion threshold is set at twenty percent and the reference point deviates twenty percent or more from the averaged value, the reference point is excluded.

At step 321, the reference point remains in the data series if it does not satisfy the reference point exclusion threshold. For example, if the reference point exclusion threshold is set at twenty percent and the reference point deviates less that twenty percent of the averaged value, the reference point remains in the data set.

At step 324, the data series is checked to determine whether additional data is available for processing. If additional data is available, at step 327, the window is moved up one data point and the control flow returns to step 309 to repeat the search for outliers. Otherwise, the control flow ends as indicated at step 395.

The above parameters (i.e., a priori exclusion threshold, window size, reference point exclusion threshold) are provided by way of example and can be adjusted to optimize the quantification of cardiopulmonary coupling as desired by the operator.

Figure 4:
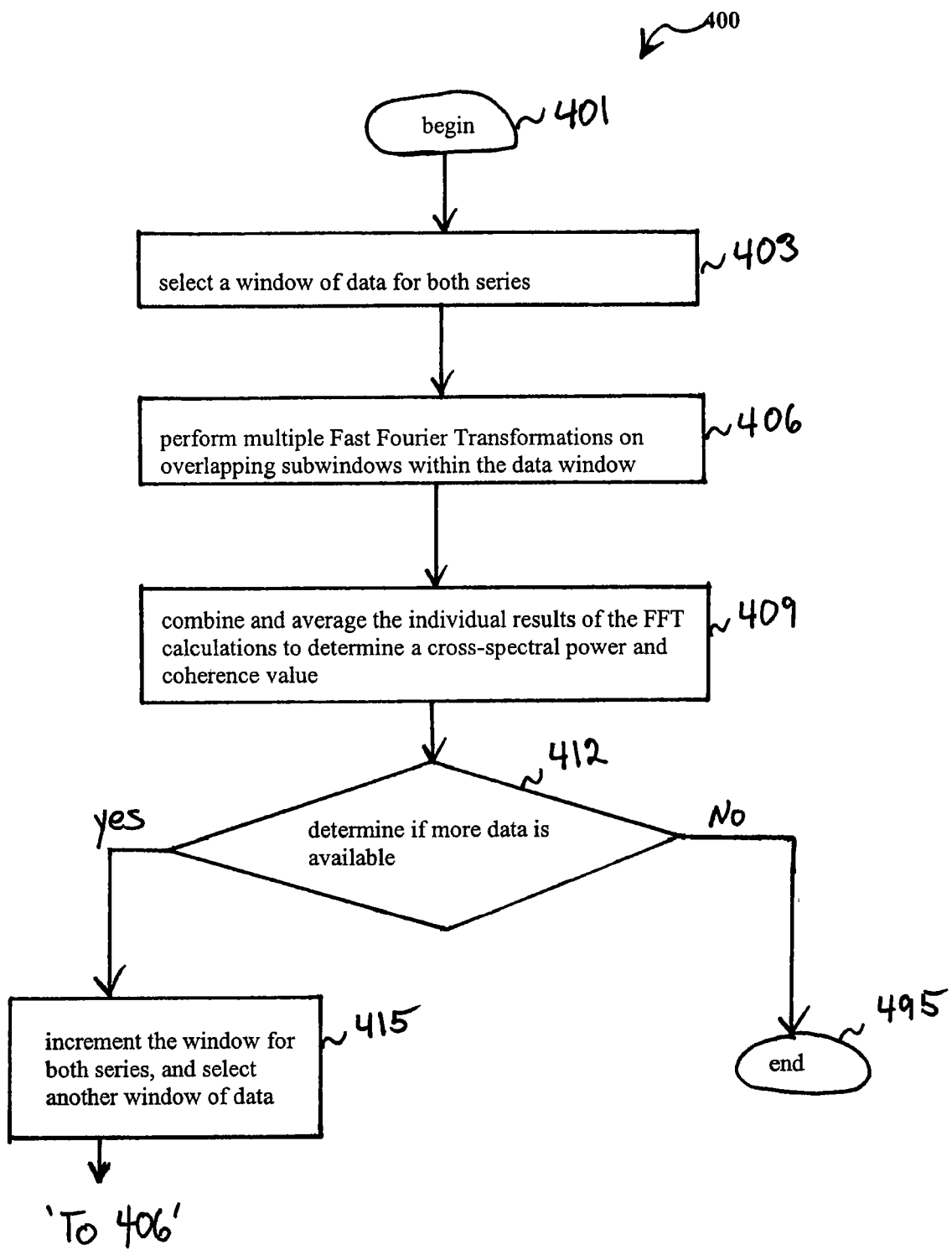
FIG. 4 illustrates an operational flow for calculating cross-spectral power and coherence according to an embodiment of the present invention.

As described above with reference to step 218, cross-spectral power and coherence are calculated for overlapping windows of data selected from, both, the NN interval series and their associated EDR series. In an embodiment, the cross-spectral power and coherence of these two signals are calculated over a 1,024 sample (e.g., approximately 8.5 minute) window using FFT applied to three overlapping 512 sample sub-windows within the 1,024 coherence window. Referring to FIG. 4, flowchart 400 represents the general operational flow of an embodiment of the present invention for calculating cross-spectral power and coherence. More specifically, flowchart 400 shows an example of a control flow for using FFT to calculate cross-spectral power and coherence of two data series.

The control flow of flowchart 400 begins at step 401 and passes immediately to step 403. At step 403, a window of data is selected.

At step 406, FFTs are performed within the selected window. In an embodiment, three FFTs are performed within the selected window. A first FFT is performed at the beginning, a second transform at the middle, and a final transform at the end of the selected window. For each FFT, the size of the frequency bin is 512 data points. The intra-window increments are 256 points for the first, second and third FFT. Thus, the sub-windows overlap by fifty percent.

At step 409, the individual results of the FFT calculations are combined and averaged to determine a cross-spectral power and coherence value. In other words, for each 1,024 window, the three FFT calculations are combined and averaged to determine the cross-spectral power and coherence for a window of data.

At step 412, it is determined whether additional data are available for further FFT calculations. If additional data are available, at step 415, the next window of data is selected and the control flow returns to step 406 to apply FFT to three overlapping 512 sample sub-windows within the selected 1,024 coherence window. In other words, the previous 1,024 window (selected at step 403) is advanced by 256 samples (e.g., approximately 2.1 minutes) and three FFT calculations are performed.

Upon completion of the calculations for the entire NN and EDR data series, the control flow ends as indicated at step 495.

FIGS. 1-4 are conceptual illustrations allowing an explanation of the present invention. It should be understood that embodiments of the present invention could be implemented in hardware, firmware, software, or a combination thereof. In such an embodiment, the various components and steps would be implemented in hardware, firmware, and/or software to perform the functions of the present invention. That is, the same piece of hardware, firmware, or module of software could perform one or more of the illustrated blocks (i.e., components or steps).

Figure 5:
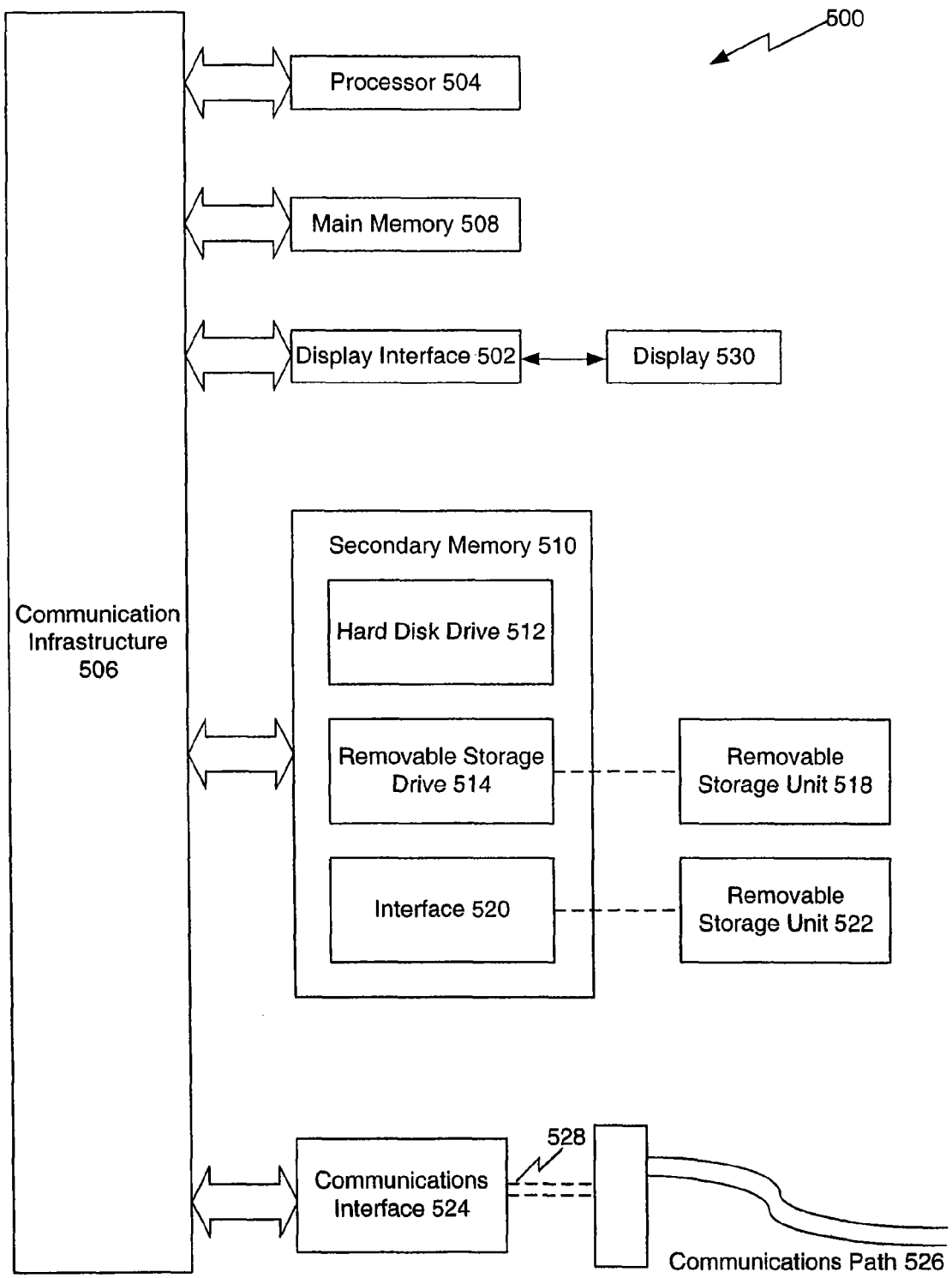
FIG. 5 illustrates an example computer system useful for implementing portions of the present invention.

The present invention can be implemented in one or more computer systems capable of carrying out the functionality described herein. Referring to FIG. 5, an example computer system 500 useful in implementing the present invention is shown. Various embodiments of the invention are described in terms of this example computer system 500. After reading this description, it will become apparent to one skilled in the relevant art(s) how to implement the invention using other computer systems and/or computer architectures.

The computer system 500 includes one or more processors, such as processor 504. The processor 504 is connected to a communication infrastructure 506 (e.g., a communications bus, crossover bar, or network).

Computer system 500 can include a display interface 502 that forwards graphics, text, and other data from the communication infrastructure 506 (or from a frame buffer not shown) for display on the display unit 530.

Computer system 500 also includes a main memory 508, preferably random access memory (RAM), and can also include a secondary memory 510. The secondary memory 510 can include, for example, a hard disk drive 512 and/or a removable storage drive 514, representing a floppy disk drive, a magnetic tape drive, an optical disk drive, etc. The removable storage drive 514 reads from and/or writes to a removable storage unit 518 in a well-known manner. Removable storage unit 518, represents a floppy disk, magnetic tape, optical disk, etc. which is read by and written to removable storage drive 514. As will be appreciated, the removable storage unit 518 includes a computer usable storage medium having stored therein computer software (e.g., programs or other instructions) and/or data.

In alternative embodiments, secondary memory 510 can include other similar means for allowing computer software and/or data to be loaded into computer system 500. Such means can include, for example, a removable storage unit 522 and an interface 520. Examples of such can include a program cartridge and cartridge interface (such as that found in video game devices), a removable memory chip (such as an EPROM, or PROM) and associated socket, and other removable storage units 522 and interfaces 520 which allow software and data to be transferred from the removable storage unit 522 to computer system 500.

Computer system 500 can also include a communications interface 524. Communications interface 524 allows software and data to be transferred between computer system 500 and external devices. Examples of communications interface 524 can include a modem, a network interface (such as an Ethernet card), a communications port, a PCMCIA slot and card, etc. Software and data transferred via communications interface 524 are in the form of signals 528 which can be electronic, electromagnetic, optical, or other signals capable of being received by communications interface 524. These signals 528 are provided to communications interface 524 via a communications path (i.e., channel) 526. Communications path 526 carries signals 528 and can be implemented using wire or cable, fiber optics, a phone line, a cellular phone link, an RF link, free-space optics, and/or other communications channels.

In this document, the terms "computer program medium" and "computer usable medium" are used to generally refer to media such as removable storage unit 518, removable storage unit 522, a hard disk installed in hard disk drive 512, and signals 528. These computer program products are means for providing software to computer system 500. The invention is directed to such computer program products.

Computer programs (also called computer control logic or computer readable program code) are stored in main memory 508 and/or secondary memory 510. Computer programs can also be received via communications interface 524. Such computer programs, when executed, enable the computer system 500 to implement the present invention as discussed herein. In particular, the computer programs, when executed, enable the processor 504 to implement the processes of the present invention, such as the various steps of methods 100, 200, 300, and 400, for example, described above. Accordingly, such computer programs represent controllers of the computer system 500.

In an embodiment where the invention is implemented using software, the software can be stored in a computer program product and loaded into computer system 500 using removable storage drive 514, hard drive 512, interface 520, or communications interface 524. The control logic (software), when executed by the processor 504, causes the processor 504 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to one skilled in the relevant art(s).

In yet another embodiment, the invention is implemented using a combination of both hardware and software.

The foregoing description of the specific embodiments will so fully reveal the general nature of the invention that others can, by applying knowledge within the skill of the art (including the contents of the documents cited and incorporated by reference herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the art.

While various embodiments of the present invention have been described above, it should be understood that they have been presented by way of example, and not limitation. It will be apparent to one skilled in the relevant art(s) that various changes in form and detail can be made therein without departing from the spirit and scope of the invention. Thus, the present invention should not be limited by any of the above-described exemplary embodiments, but should be defined only in accordance with the following claims and their equivalents.

What is claimed is:

1. A method of evaluating a subject's sleep quality, comprising:
    accessing a first series of physiological data representing respiration data of the subject;
    accessing a second series of physiological data representing cardiac data of the subject, said second series being temporally aligned with said first series;
    calculating a data series of coherent cross power based on the first and second series by determining a cross-spectra power and a coherence for each of a plurality of temporally aligned subsets of data from said first series and said second series and computing said coherent cross power for each temporally aligned subset, said coherent cross power being computed from the product of said cross-spectra power and said coherence of each temporally aligned subset;
    determining cardiopulmonary coupling from the data series of coherent cross power; and
    comparing the cardiopulmonary coupling to a detection threshold associated with sleep quality,
    wherein the method is executed in a processor of a computer system.

2. The method according to claim 1,
    wherein the calculating a data series of coheren cross power includes using a Fast Fourier Transform.

3. The method according to claim 1, further comprising:
    determining cyclic alternating pattern (CAP) activity, non-CAP activity, wake activity, REM activity, or a sleep breathing disorder based on the comparison between the cardiopulmonary coupling and the detection threshold.

4. The method according to claim 1, wherein the first and second series of physiological data are derived from an electrocardiogram signal.

5. The method according to claim 1, wherein said accessing a first series comprises:
    extracting a series of QRS amplitude data from said physiological data.

6. The method according to claim 1, wherein said accessing a second series comprises:
    extracting a series of normal-to-normal heart beats from said physiological data.

7. A computer program product having a computer useable medium with computer readable program code functions embedded in said medium for causing a computer to evaluate sleep quality, comprising:
    a first computer readable program code function that causes the computer to access a first series of physiological data;
    a second computer readable program code function that causes the computer to access a second series of physiological data, said second series being temporally aligned with said first series; and
    a third computer readable program code function that causes the computer to calculate a data series of coherent cross power based on the first and second series by determining a cross-spectra ower and a coherence for each of a plurality of temporally aligned subsets of data from said first series and said second series and computing said coherent cross power for each temporally all aligned subset, said coherent cross power being computed from the product of said cross-spectra power and said coherence of each temporally aligned subset;
    a fourth computer readable program code function that causes the computer to determine cardiopulmonary coupling from the data series of coherent cross power; and
    a fifth computer readable program code function that causes the computer to compare the cardiopulmonary coupling to a detection threshold associated with sleep quality.

8. A method of evaluating sleep, comprising:
    accessing a first series of physiological data;
    accessing a second series of physiological data, said second series being temporally aligned with said first series;
    calculating a data series of coherent cross power based on the first and second series of physiological data by computing a product of a cross-spectra power and a coherence calculation of the first and second series; and
    comparing the data series of coherent cross power to a detection threshold associated with sleep quality,
    wherein the method is executed in a processor of a computer system.

9. The method according to claim 8, wherein the comparing the data series of coherent cross power includes:
    calculating a ratio of coherent cross power between two frequency bands based on the calculated data series of coherent cross power.

10. The method according to claim 9,
    wherein the two frequency bands include a low frequency (LF) band and a high frequency (HF) band.

11. The method according to claim 8, wherein the comparing the data series of coherent cross power includes:
    determining a minimum low frequency (LF) power.

12. The method according to claim 8, wherein the first and second series of physiological data are derived from a single physiological signal measured from a subject.

13. The method according to claim 12, wherein the single physiological signal is an electrocardio gram signal.

14. The method according to claim 8, wherein said accessing a first series comprises:
    extracting a series of QRS amplitude data from said physiological data.

15. The method according to claim 8, wherein said accessing a second series comprises:
    extracting a series of normal-to-normal heart beats from said physiological data.

16. A method of evaluating a subject's sleep, comprising:
    accessing a first series of physiological data representing respiration data of the subject;
    accessing a second series of physiological data representing cardiac data of the subject, said second series being temporally aligned with said first series;
    calculating a data series of coherent cross power based on the first and second series of physiological data, wherein the data series of coherent cross power is calculated by calculating a product of a cross-spectra power and a coherence calculation of the first and second series; and
    comparing the data series of coherent cross power to a detection threshold associated with sleep quality,
    wherein the method is executed in a processor of a computer system.

17. The method according to claim 16, wherein said accessing a first series comprises:
    extracting a series of QRS amplitude data from said physiological data.

18. The method according to claim 16, wherein said accessing a second series comprises:
    extracting a series of normal-to-normal heart beats from said physiological data.

* * * * *

UNITED STATES PATENT AND TRADEMARK OFFICE
CERTIFICATE OF CORRECTION

PATENT NO. : 8,403,848 B2
APPLICATION NO. : 12/018768
DATED : March 26, 2013
INVENTOR(S) : Mietus et al.

Page 1 of 1

It is certified that error appears in the above-identified patent and that said Letters Patent is hereby corrected as shown below:

In the Claims

Column 11, Line 12, replace "being," with --being--.

Column 11, Line 30, replace "coheren" with --coherent--.

Column 11, Line 62, replace "ower" with --power--.

Column 12, Line 35, replace "electrocardio gram" with --electrocardiogram--.

Signed and Sealed this
Twenty-first Day of May, 2013

Teresa Stanek Rea
*Acting Director of the United States Patent and Trademark Office*